United States Patent [19]

Hayes et al.

[11] 4,432,225
[45] Feb. 21, 1984

[54] DETECTION SYSTEM FOR A GAS CHROMATOGRAPH

[75] Inventors: John M. Hayes; Gerald J. Small, both of Ames, Iowa

[73] Assignee: The United States of America as represented by the United States Department of Energy, Washington, D.C.

[21] Appl. No.: 371,743

[22] Filed: Apr. 26, 1982

[51] Int. Cl.³ ............................................. G01N 31/08
[52] U.S. Cl. ................................... 73/23.1; 250/458.1; 250/459.1
[58] Field of Search ...................... 73/23.1; 250/458.1, 250/459.1, 461.1; 356/317, 318; 422/89, 91

[56] References Cited

U.S. PATENT DOCUMENTS 4,100,412 7/1978 Hausdorff .......................... 250/458.1
4,350,661 9/1982 Davis et al. ........................ 250/458.1

Primary Examiner—Stephen A. Kreitman
Attorney, Agent, or Firm—Sandra B. Weiss; John M. Albrecht; Richard G. Besha

[57] ABSTRACT

A method and apparatus are described for the quantitative analysis of vaporizable compounds, and in particular of polycyclic aromatic hydrocarbons which may be induced to fluoresce. The sample to be analyzed is injected into a gas chromatography column and is eluted through a narrow orifice into a vacuum chamber. The free expansion of the eluted sample into the vacuum chamber creates a supersonic molecular beam in which the sample molecules are cooled to the extent that the excited vibrational and rotational levels are substantially depopulated. The cooled molecules, when induced to fluoresce by laser excitation, give greatly simplified spectra suitable for analytical purposes. The laser induced fluorimetry provides great selectivity, and the gas chromatograph provides quantitative transfer of the sample to the molecular beam.

13 Claims, 4 Drawing Figures

DETECTION SYSTEM FOR A GAS CHROMATOGRAPH

CONTRACTUAL ORIGIN OF THE INVENTION

The U.S. Government has rights in this invention pursuant to Contract No. W-7405-ENG-82 between the U.S. Department of Energy and Ames Laboratory.

BACKGROUND OF THE INVENTION

This invention relates to an apparatus and method for quantitatively analyzing a sample containing vaporizable molecules. The invention further relates to an apparatus and method for quantitatively analyzing organic pollutants such as polycyclic aromatic hydrocarbons.

One of the most difficult problems in analytical chemistry in recent years has been the quantitative analysis of minute amounts of organic pollutants. These pollutants derive from a variety of sources including energy resources, the chemical industry, and agricultural land. One significant class of organic pollutants is the polycyclic aromatic hydrocarbons (PAH's) generated from coal, synthetic fuel and shale oil. These compounds may have mutagenic and carcinogenic properties which are strongly dependent on isomeric structure and substitution; thus it would be highly desirable to be able to quantitatively analyze a sample for substitutional isomers of PAH's. However, substitutional isomers of PAH's often have very similar chemical and physical properties which greatly complicates their separation, identification, and quantitation.

Limited success on the quantitative analysis of organic pollutants has been achieved through gas chromatography (GC). Gas chromatography is a well-known and versatile tool for the separation and quantitative analysis of vaporizable compounds. In a typical gas chromatograph, a vaporizable sample is injected into a long narrow column containing a stationary liquid phase supported on an inert solid matrix. The sample is vaporized at the injection port and carried through the column by an inert mobile gaseous phase. The components of the sample are fractionated as a consequence of partition between the liquid and gaseous phases as they migrate along the column. The rate at which the various components migrate along the column depends upon their tendency to dissolve in the stationary liquid phase. As the components are eluted from the column they are detected by any of a variety of standard methods, such as thermal conductivity or flame ionization. The detector sends a signal to a chart recorder which records each eluted compound as a peak. Qualitative identification of the components is based upon the retention times, defined as the time required for peaks to appear at the end of the column. Quantitative data are obtained from evaluation of peak areas.

It may be seen that the success of a chromatographic separation depends on the different solubilities of the components of the mixture to be analyzed in the stationary liquid phase. Because substitutional isomers of PAH's often have almost identical solubilities, they usually cannot be resolved on a standard gas chromatograph. Thus gas chromatography is not satisfactory as an analytical tool for many PAH mixtures.

It is well known that most PAH's as well as other $\pi$-electron molecules have fluorescent spectra characteristic of their structure and substitution. However, conventional room temperature solution spectra of many PAH's are not sufficiently well resolved to permit identification of the constituents of a complex mixture. This is due to the broad fluorescence vibronic bands produced, in part, by thermal molecular motions and coupling with liquid phonon modes. Even in the gas phase, PAH spectra are broad and complicated; in this case due to spectral congestion of rotational, sequence and hot bands. Thus ordinary fluorescence spectra can not be used to analyze gaseous PAH eluants from a gas chromatograph.

Rotationally cooled laser induced fluorescence (RC-LIF) is a technique used to study interacting molecular systems cooled to near 0° K. in a supersonic molecular beam. By this method, either a gas sample or a liquid or solid sample with a high vapor pressure is placed in a chamber to provide a reservoir of gaseous sample molecules. The chamber may be heated if necessary to increase the gas pressure of the sample molecules. The sample molecules are seeded into a flow of helium, and the seeded helium is allowed to freely expand through a very small orifice in the reservoir chamber into a vacuum chamber to form a supersonic molecular beam. Within the beam a finite number of binary collisions occur which narrow the velocity distribution of the jet and cool the vibrational and rotational degrees of freedom of the seed molecules. By this method, the supersonic beam provides an intense source of seed molecules traveling in a vacuum with an extremely narrow velocity distribution, completely isolated from other particles and cooled to such an extent that the excited rotational and vibrational levels of the seed molecules are substantially depopulated. High resolution dye lasers may then be used to induce electronic transitions in the seed molecules with near unit probability. In those cases in which the laser-excited molecule fluoresces, a greatly simplified high-resolution spectrum can be obtained, with rotational and vibrational absorptions almost completely eliminated. The high sensitivity of fluorescent detection together with the high efficiency of laser excitation combine to produce large signals in spite of the otherwise prohibitively low density of the molecular beam.

RC-LIF has been used to obtain new spectroscopic data on a number of molecules. The theory and applications of RC-LIF are discussed in detail in "Laser Spectroscopy in Supersonic Jets" by Levy et al, *Chemical and Biochemical Application of Lasers*, Vol. II, edited by C. Bradley Moore, 1977, Academic Press, pages 1–41. Despite the tremendous potential of this technique, it has heretofore been limited to the acquisition of physical and spectroscopic data. Because the seeded beam must be continuously emitted from a reservoir, it has been impossible to quantify the amount of fluorescent seed material in the beam. In addition, it may require several hours to attain a spectrum of a single sample. Therefore this method has heretofore been unavailable as a tool for quantitative chemical analysis.

SUMMARY OF THE INVENTION

It is thus one object of the invention to provide a method and apparatus for analyzing vaporizable compounds.

It is another object of the invention to provide a method and apparatus for analyzing vaporizable compounds eluted from a gas chromatograph.

It is yet another object of the inventin to provide a method and apparatus for quantitatively analyzing vaporizable compounds eluted from a gas chromatograph which may be induced to emit characteristic spectra.

It is still another object of the invention to provide a method and apparatus for quantitatively analyzing vaporizable compounds eluted from a gas chromatograph which have characteristic fluorescent spectra.

Additional objects, advantages, and novel features of the invention will be set forth in part in the following description.

We have invented a new method and apparatus for quantitatively analyzing minute amounts of PAH's. We have found that when a gas chromatograph column is used to provide efficient quantitative transfer of a PAH sample for rotationally cooled laser induced fluorescense spectroscopy, we can achieve unprecedented accuracy and sensitivity in the quantitative analysis of substitutional isomers of PAH's. In accordance with the invention, a column suited for gas chromatography work is packed with an appropriate separation medium. The column is fitted on one end with a means for injecting a sample and at the other end with a narrow diameter nozzle or orifice through which the chromatographed sample will elute. The column is provided with a flow of helium which elutes the sample from the injection end through the column and out through the orifice. The orifice is positioned to elute the sample into a vacuum chamber, such that molecules eluted from the orifice expand into the chamber to form a supersonic molecular beam. The supersonic expansion of the sample molecules in the flowing helium allows the sample molecules to rotationally cool as previously described. The vacuum chamber is fitted with a laser-permeable inlet window positioned so that a beam of laser light can intersect the supersonic molecular beam. An exit window is provided through which the laser-induced fluorescence of the supersonic beam can be detected. The apparatus thereby incorporates laser induced fluorimetry as a highly sensitive detector with a gas chromatograph.

This device provides a unique methodology for the analytical determination of fluorescent molecules, and especially for organic pollutants. The gas chromatograph provides quantitative transfer of the sample into the supersonic molecular beams. Compounds such as PAH's which cannot always be separated from each other on a gas chromatograph but which absorb at different wavelengths can be analyzed accurately at sub-microgram levels by preselecting the proper laser excitation wavelength. For example, the laser may be tuned to a wavelength where only a few selected compounds absorb, or a fixed-frequency laser may be used at a frequency where all members of a class of compounds absorb. Sample turnaround time can be reduced to a few minutes or less.

DETAILED DESCRIPTION OF THE PREFERRED EMBODIMENT

The following is a description of a preferred embodiment; other embodiments will be readily apparent to those skilled in the art.

Figure 1:
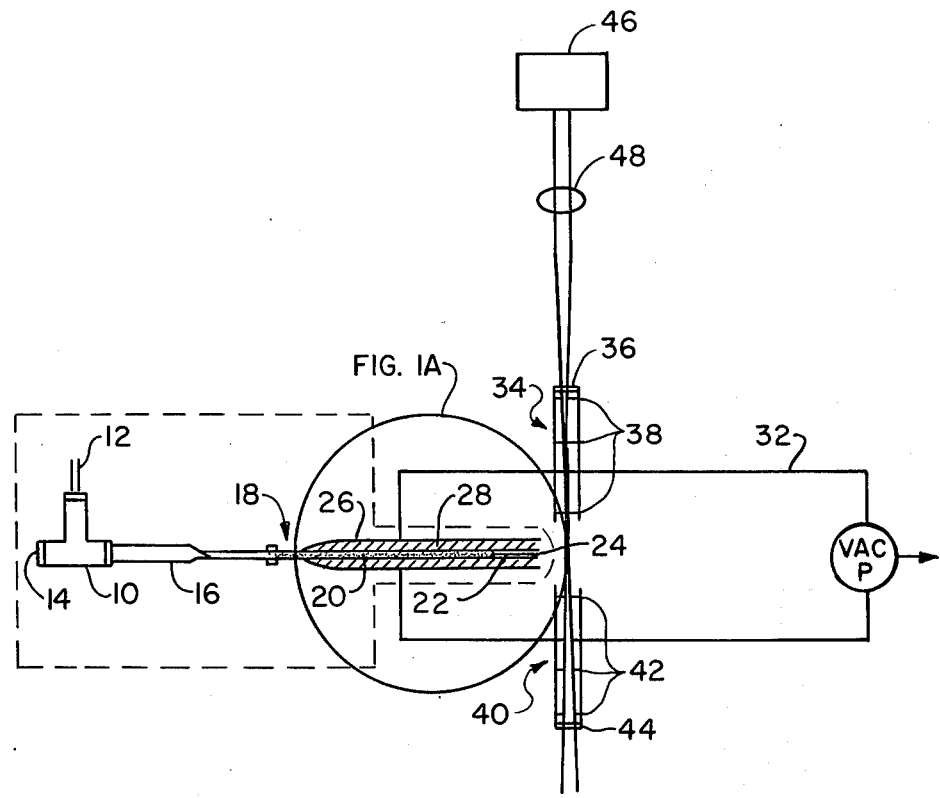
FIG. 1 is a schematic diagram of the inventive apparatus.
Figure 1A:
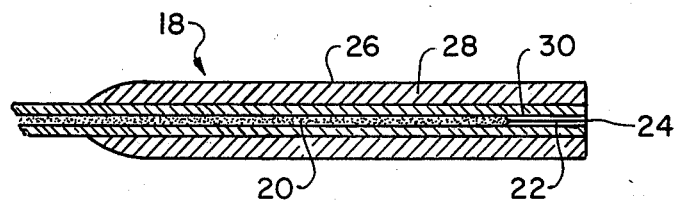
FIG. 1A is an enlarged portion of FIG. 1.

FIG. 1 is a schematic diagram of a gas chromatograph (GC) column, enclosed in the dotted line, positioned to interface with a rotationally cooled-laser induced fluorescence (RC-LIF) system. FIG. 1A is a magnified view of the GC supersonic nozzle and heaters. As seen in the figures, a simple stainless steel T-fitting 10 may accommodate both the helium inlet 12 and a sample injection port 14. The T-fitting may be heated by any conventional means such as heating tape to a temperature sufficiently high to instantly vaporize the injected sample. The vaporized sample is carried by the flowing helium through heated glass tubing 16 to the packed gas chromatography column 18.

The column 18 may typically comprise 8" of 8-mm o.d. glass tubing 20 and 2" of 1-mm o.d. capillary tubing 22 which terminates in a 150 $\mu$m orifice 24. The column 18 is packed with a high temperature silicone oil supported on an inert solid matrix, useful for separating polycyclic aromatic hydrocarbons. The column 18 is housed in a copper oven 26, and is supported therein by a centering and insulating cylinder 28. Heaters 30 are used to maintain the column at a temperture sufficient to prevent condensation of the sample. The injection port 14 is maintained at about 180° C. to ensure instant vaporization of the sample. The exposed glass tubing 16 is heated with heating tape to about 130° C., and the heaters 30 maintain the packed column 18 at about 85° C.

The chromatography column 18 extends into a vacuum chamber 32. As the stream of helium and sample molecules is eluted from capillary tubing 22 through narrow orifice 24, it expands into vacuum chamber 32 as a supersonic molecular beam. In accordance with the theory of supersonic expansion as previously discussed and referenced, the sample molecules are rapidly cooled in their vibrational and rotational modes of motion. At some point downstream from orifice 24 the velocity distribution of the molecular beam becomes uniform. Downstream of this point, vacuum chamber 32 is provided with two window assemblies 34 and 40. Each assembly comprises laser permeable windows and light baffles. A beam of laser light from laser source 46 passes through focusing lens 48, inlet window 36 and light baffles 38 to intersect the supersonic molecular beam. The laser beam exits vacuum chamber 32 through light baffles 42 and exit window 44 to a reference phototube, not shown in the Figure. If the laser is tuned to a frequency at which one or more components of the sample fluoresce, this fluorescence may be detected and measured according to methods well known in the art. The fluorescense is typically measured along a line perpendicular to both the molecular beam and the laser beam. The intensity of the fluorescence peak at a particular wavelength may then be used as a quantitative measure of the components in the sample that absorb at that wavelength. Components which fluoresce at the same wavelength and have different retention times may be analyzed on a single chromatogram. Components which have the same retention time but which fluoresce at different wavelengths may be analyzed on separate chromatograms, even if the spectra would normally not be resolvable by conventional fluorescent spectroscopy or gas chromatographic techniques. Typical sample turnaround times are on the order of two minutes or less.

The following examples illustrate some of the unique capabilities of the instant invention.

EXAMPLE I

A gas chromatography column as previously described was packed with 3% OV®101, Ohio Valley, Inc., silicone oil on 80-100 mesh Chromosorb® (Johns-Manville, Inc.) prepared by Alltech®. The column was interfaced with a vacuum chamber equipped for laser fluorimetry. The excitation source was the frequency doubled output of a Quanta-Ray PDL-1 dye laser pumped by a DCR-1 Nd:YAG laser. The laser beam crossed perpendicular to the supersonic molecular beam 5 mm from the orifice. The resulting fluorescence was collected at right angles to both beams by an F/2.5 lens and then focussed into a 0.3 m, F/4.2 monochromator. The monochromator was set at 341.5 nm with a bandpass of 7.5 nm; many PAH's exhibit fairly broad emission bands in this region. Signals from both the monochromator phototube and a normalizing reference tube were detected with pulse stretching preamplifiers and measured by a Molectron LP20 laser photometer.

Figure 2:
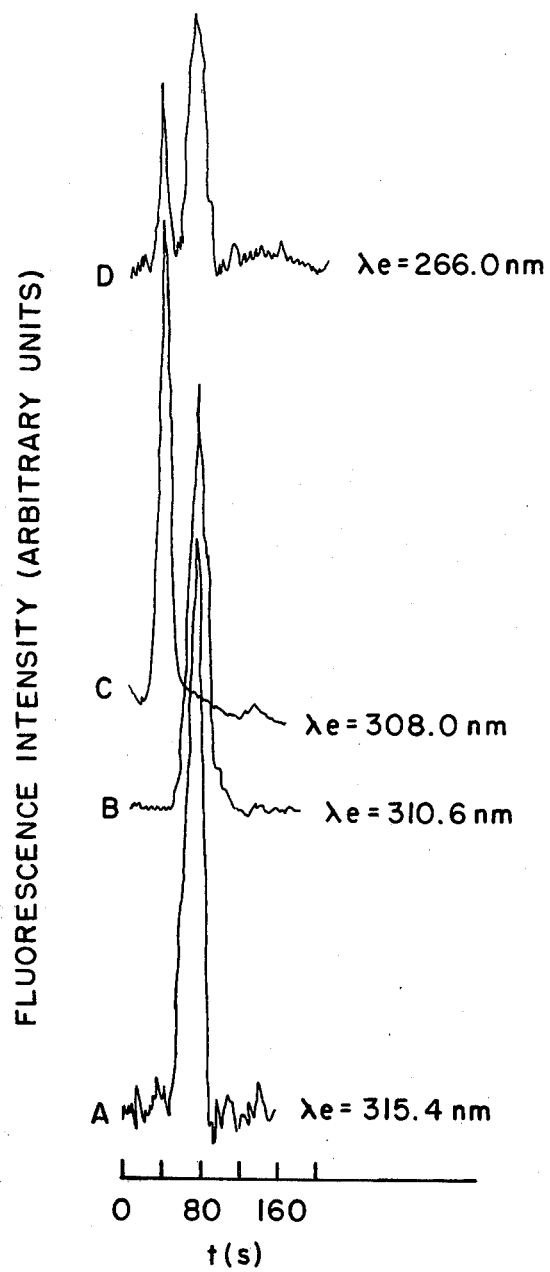
FIG. 2 is a set of chromatograms of an equimolar mixture of naphthalene, $\alpha$-methylnaphthalene, and $\beta$-methylnaphthalene at four different excitation wavelengths.

Several samples of solutions of $\beta$-methylnaphthalene in various concentrations in cyclohexane were run through the RC-LIF-GC apparatus. Laser excitation was set at 315.4 nm which is specific for $\beta$-methylnaphthlene. The peaks were symmetrical and well-resolved. The retention time was about 80 s. It was found that peak height varied linearly with the amount injected from $5 \times 10^{-8}$g to $1.4 \times 10^{-5}$g. The linearity is not changed even when the sample is mixed with a 1000-fold excess of $\alpha$-methylnaphthalene which elutes simultaneously. A chromatogram of an equimolar mixture of $\beta$-methylnaphthalene,$\alpha$-methylnaphathlene and naphthalene, excited at 315.4 nm is shown in FIG. 2A. It can be seen that no signal was detected for either of the added molecules.

EXAMPLE II

Several samples of $\alpha$-methylnaphthalene in various concentrations in cyclohexane solution were run through the same RC-LIF-GC apparatus as described in Example I. Laser excitation was set at 310.6 nm which is specific for $\alpha$-methylnaphthalene. These peaks were also symmetrical and well-resolved, and had the same retention time as the $\beta$-methylnaphthalene peak. As with the $\beta$-isomer, the peak height varies linearly with the amount of the $\alpha$-isomer in the sample. FIG. 2B is a chromatogram of the same equimolar solution of $\alpha$-methylnaphthalene, $\beta$-methylnaphthalene, and naphthalene but excited at 310.6 nm. A signal is seen only for the $\alpha$-isomer.

EXAMPLE III

Several samples of naphthalene at various concentrations in cyclohexane solution were run through the same RC-LIF-GC apparatus described in Example I. Laser excitation was set at 308.0 nm which is specific for naphthalene. The peaks were sharp and well resolved. The retention time was about 45 seconds. As with the methyl-substituted naphthalenes, the signal varied linearly with the amount of naphthalene in the sample even in a 100-fold excess of the substituted naphthalenes. FIG. 2C is a chromatogram of the equimolar solution used in the previous examples but excited at 308.0 nm. At this wavelength no signal is detected for either of the methyl-substituted naphthalenes.

EXAMPLE IV

FIG. 2D shows a chromatogram of the equimolar mixture of naphthalene and the $\alpha$- and $\beta$-substituted isomers run through the same RC-LIF-CG apparatus with the laser excitation set at 266.0 nm. This wavelength is non-specific in that it induces fluorescence in all three molecules. Two peaks are seen on the chromatogram at 45 s and 80 s. From the previous examples these may be assigned to naphthalene and the $\alpha$- and $\beta$-methylnaphthalenes, respectively. The intensity of the latter peak is equal to the sum of the intensities of the two species when each is injected separately. At this wavelength the methylnaphthalenes are not resolved and cannot each be determined quantitatively, but they may be detected and their sum determined quantitatively. The naphthalene peak is resolved by virtue of its shorter retention time on the chromatography column and thus may be determined quantitatively.

Examples I-IV illustrate the feasibility of quantitative determination of PAH's by RC-LIF-GC. Compounds may be quantitatively analyzed which have heretofore never been resolvable by either chromatography or conventional fluorescence techniques. For the naphthalenic system studied, the minimum and maximum detection limits for each compound are listed in Table I. The data show that detection of sample sizes on the order of 10 ng is achievable. Also included in the table is the correlation coefficient, R, obtained in a least squares fit of peak height versus weight injected. For naphthalene and $\alpha$-methylnaphthalene the maximum amounts detectable were determined by column characteristics. Injection of larger amounts led to broadening and asymmetry of the chromatogram peak. The lower maximum observed for $\beta$-methylnaphthalene marks the point at which the calibration curve, peak height versus weight, becomes sublinear.

TABLE I

| Detection limits and correlation coefficients for $\beta$-methylnaphthalene and $\alpha$-methylnaphthalene | | | |
|---|---|---|---|
| | Lower Limit (g) | Upper Limit (g) | R |
| Naphthalene | $6.0 \times 10^{-8}$ | $1.2 \times 10^{-4}$ | .986 |
| $\beta$-methylnaphthalene | $1.4 \times 10^{-8}$ | $1.1 \times 10^{-5}$ | .996 |
| $\alpha$-methylnaphthalene | $4.0 \times 10^{-8}$ | $1.4 \times 10^{-4}$ | .972 |

This method and apparatus have been proven workable not only for samples prepared in the laboratory but for typical industrial samples as well, as illustrated in the following example.

EXAMPLE V

Figure 3:
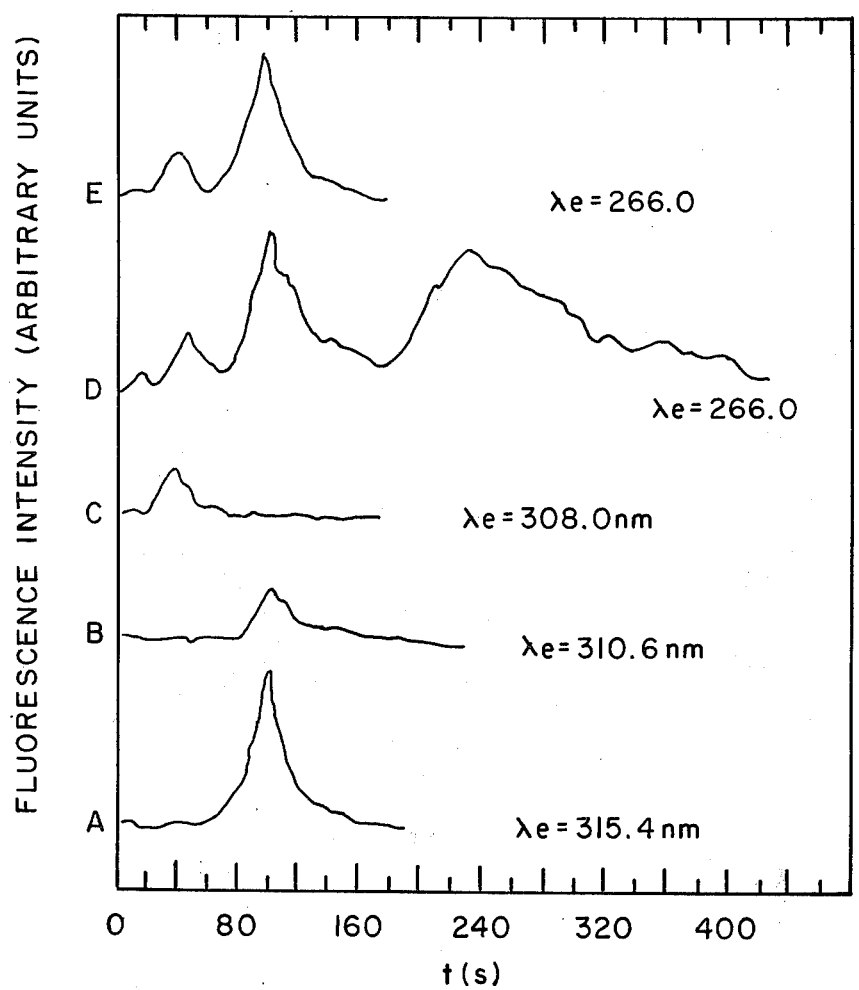
FIG. 3 is a set of chromatograms of a sample of crude oil at the four excitation wavelengths used in FIG. 2, and of a laboratory prepared mixture of naphthalene, $\alpha$-methylnaphthalene, and $\beta$-methylnaphthalene at the concentrations determined for the crude oil sample.

A 0.5 ml aliquot of crude oil was diluted to 1.5 ml with cyclohexane. Samples of this solution were injected into the same apparatus used for the previous four examples. Chromatograms obtained with the laser excitation wavelength set at 315.4 nm, 310.6 nm, and 308.0 nm are shown in FIGS. 3A, 3B, and 3C respectively. Each of these show a single peak corresponding to $\beta$-methylnaphthalene,$\alpha$-methylnaphthalene, and naphthalene, respectively; the retention times for each compound are those expected from the chromatograms of the pure samples. FIG. 3D is a chromatogram of the crude oil solution with the excitation wavelength set at 266.0 nm. The naphthalene and methylnaphthalene peaks are clearly seen in addition to a number of other peaks with longer retention times. From these chromatograms the amounts of each of the three compounds in the crude oil can be quantitatively determined. Table II summarizes the amounts of the three compounds found in the crude oil, as well as the amounts of the other two compounds detected in each of the "pure" materials.

TABLE II

Amounts (mg/g) of naphthalene, β-methylnaphthalene and α-methylnaphthalene determined in crude oil and in each other

|  | Crude Oil | Naphthalene | β-MN | α-MN |
|---|---|---|---|---|
| Naphthalene | .19 | — | N | N |
| β-methylnaphthalene | .53 | .045 | — | 5.0 |
| α-methylnaphthalene | .26 | 3. | 12.0 | — |

N = not determined

EXAMPLE VI

As a check on the results determined for the crude oil sample, a laboratory sample was prepared with the three compounds in the same proportion as determined to be in the crude oil. FIG. 3E shows the chromatogram of this sample at 266.0 nm, the non-specific wavelength. It may be seen that the chromatogram is virtually identical in the pertinent region to that obtained for the crude oil sample. This is a clear indication of the reliability of the RC-LIF-GC system for the quantitative determination of PAH's in industrial samples.

RC-LIF-GC is a simple, practical analytical technique which offers a new and unique approach to the quantitative determination of molecules in mixtures. The remarkable selectivity is due to the RC-LIF and the quantitative ability is due to the GC. The data show that a detection limit of ~10ng is achievable for naphthalenic system, but even smaller quantities may be detected with simple modifications. For example, in these examples the detection monochromator wavelength was chosen for convenience to be in a region where all three molecules emit. This is, however, a region of weak emission. The sensitivity for each molecule could be greatly improved by choosing an optimum detection wavelength setting for each molecule.

Other improvements could be achieved by modifying the apparatus. For example, the largest increase in sensitivity can be achieved by increasing the excitation duty cycle, which may be generally defined as the length of time in which data is collected from fluorescing molecules. The apparatus described above employed a continuous flow nozzle and pulsed laser. Use of a pulsed nozzle synchronized to the laser pulses would increase the duty cycle by $10^3$. This would increase the efficiency of the data collection and lower the minimum detectable amount of material still further.

Still other apparatus modifications would improve both the capability and convenience of the invention. The sensitivity can be increased by a factor of approximately 10 by using a planar supersonic jet rather than a circular nozzle. Commercially available GC columns and chromatographic systems may be used instead of the short column described above, especially if there are many components in a sample which can be separated. Use of rapid scan spectrometers, which could scan a range of excitation wavelengths, would allow the simultaneous analysis of components with the same retention time such as α- and β-methylnaphthalene.

In addition to apparatus modifications, the method can be improved with an understanding of the chemical and fluorimetric properties of the species being determined. For example, the naphthalenes used here to illustrate the invention are relatively weak absorbers; molecules that are strongly absorbing would have significantly improved detection limits. Another advantage of fluorimetry is that non-fluorescent molecules can be made to fluoresce by derivatization, as is known to one skilled in the art.

Still other modifications will be readily apparent to those skilled in the arts of spectroscopy and gas chromatography. The embodiment and examples were chosen in order to best explain the principle of the invention and its practical applications.

The embodiments of this invention in which an exclusive property or privilege is claimed are defined as follows:

1. A method for quantitatively analyzing a sample of vaporizable molecules comprising
   providing a gas chromatography column,
   vaporizing said sample,
   eluting said vaporized sample through said column,
   cooling said eluted sample to substantially depopulate the excited rotational and vibrational levels of the sample molecules while said sample molecules remain vaporized,
   irradiating said cooled sample to induce the sample to emit characteristic spectral peaks, and
   determining the intensity and retention times of said characteristic spectral peaks, said intensity and retention times being indicative of the quantitative analysis of said sample.

2. The method of claim 1 wherein said cooling is accomplished by allowing said eluted sample to expand through an orifice into a vacuum chamber as a supersonic molecular beam.

3. The method of claim 2 wherein said cooled sample is irradiated by means of a laser beam.

4. The method of claim 3 wherein said characteristic spectral peaks are fluorescence spectra.

5. The method of claim 4 wherein said sample contains polycyclic aromatic hydrocarbons.

6. The method of claim 2 wherein said orifice is formed from the outlet of said chromatography column.

7. The method of claim 2 wherein the sample is carried through the column by helium gas which also expands into the vacuum chamber.

8. An apparatus for quantitatively analyzing a sample of vaporizable molecules comprising
   means for vaporizing said sample,
   a gas chromatography column,
   means for eluting said vaporized sample throughsaid gas chromatography column,
   means for cooling said eluted sample to substantially depopulate the excited rotational and vibrational levels of the sample molecules while said sample molecules remain vaporized,
   means for irradiating said cooled sample to induce the sample to emit characteristic spectral peaks,
   means for determining the intensity and retention time of said characteristic peaks.

9. The apparatus of claim 8 wherein the means for cooling said eluted sample comprises
   a vacuum chamber, and
   an orifice through which the eluted sample expands from the chromatography column into the vacuum chamber as a supersonic molecular beam.

10. The apparatus of claim 9 wherein said means for eluting said sample is a flow of helium maintained through said column, and wherein said helium also expands into the vacuum chamber.

11. The apparatus of claim 10 wherein said orifice is the outlet of said chromatography column.

12. The apparatus of claim 10 wherein the means for irradiating the sample is a laser beam.

13. The apparatus of claim 12 wherein the vacuum chamber is fitted with laser permeable inlet and outlet windows to allow irradiation of the sample.

* * * * *